United States Patent [19]

Dull et al.

[11] Patent Number: 4,859,609
[45] Date of Patent: Aug. 22, 1989

[54] NOVEL RECEPTORS FOR EFFICIENT DETERMINATION OF LIGANDS AND THEIR ANTAGONISTS OR AGONISTS

[75] Inventors: Thomas J. Dull; Heimo Riedel; Axel Ullrich, all of San Francisco, Calif.

[73] Assignee: Genentech, Inc., South San Francisco, Calif.

[21] Appl. No.: 857,899

[22] Filed: Apr. 30, 1986

[51] Int. Cl.$^4$ ................. G01N 33/566; G01N 33/542
[52] U.S. Cl. ....................... 436/501; 435/7; 436/63; 436/503; 436/537; 530/402; 530/806; 530/808; 935/81; 935/109
[58] Field of Search ................. 435/7; 436/503, 537, 436/501-563; 935/81, 109; 530/402, 806, 808

[56] References Cited

U.S. PATENT DOCUMENTS

| | | | |
|---|---|---|---|
| 3,935,074 | 1/1976 | Rubenstein et al. | 435/7 |
| 4,363,758 | 12/1982 | Masuko et al. | 935/107 X |
| 4,374,925 | 2/1983 | Litman et al. | 435/5 |
| 4,504,587 | 3/1985 | Timpl et al. | 436/538 |
| 4,544,629 | 10/1985 | Rice et al. | 436/503 X |
| 4,595,655 | 6/1986 | Self | 436/537 X |

FOREIGN PATENT DOCUMENTS

| | | |
|---|---|---|
| 0125023 | 11/1984 | European Pat. Off. |
| 0173494 | 3/1986 | European Pat. Off. |
| 3100061 | 8/1982 | Fed. Rep. of Germany |
| 2071671 | 9/1981 | United Kingdom |

OTHER PUBLICATIONS

Cobb et al., Biochem. Biophys. Acta, 738: 1-8 (1984).
Siegel et al., J. Biol. Chem., 256(17): 9266-9273 (1981).
Emr et al., J. Cell Biol., 86: 701-711 (1980).
Coulton et al., J. Bacteriol. 165(1):181-192 (1986).
Steiner et al., Methods in Enzymology, 109: 346-350 (1985).
Prywes R. et al., "EMBO Journal", 5(9): 2179-2190 (Sep. 1986).
Riedel, H. et al., "Science", 236: 197-200 (Apr. 1987).
Riedel, H. et al., "Nature", 324(6092): 68-70 (Nov. 1986).
Kris, R. M. et al., "Cell", 40: 619-625 (Mar. 1985).
Livneh, E. et al., "J. Biol. Chem.", 261(27): 12490-12497 (Sep. 1986).
Ullrich, A. et al., "Leukemia: Recent Advances in Biology and Treatment", Alan R. Liss, Inc., pp. 277-292 (1985).
Ullrich, A. et al., "Cancer Cells 3/Growth Factors & Transformation", Cold Springs Harbor Laboratory (Jun. 1985), pp. 1-9.
Hunter T., "Nature", 313: 740-741 (Feb. 1985).
Ullrich, A. et al., "Nature", 313: 756-761 (Feb. 1985).
King, G. et al., "J. Biol. Chem.", 267(14): 10869-10873 (1982).

Primary Examiner—Robert J. Warden
Assistant Examiner—Richard Wagner
Attorney, Agent, or Firm—Max D. Hensley

[57] ABSTRACT

Hybrid receptors are provided that comprise (a) the ligand binding domain of a predetermined receptor and (b) a heterologous reporter polypeptide. The hybrid receptors are useful for convenient and large scale assay of biologically active ligands or their antagonists or agonists.

15 Claims, 6 Drawing Sheets

NOVEL RECEPTORS FOR EFFICIENT DETERMINATION OF LIGANDS AND THEIR ANTAGONISTS OR AGONISTS

This invention relates to methods for screening candidate drugs for their ability to bind a receptor in such a fashion as to mimic or antagonize the function of a ligand which ordinarily interacts with the receptor in vivo. It also relates to methods for the functional assay of ligands.

Receptors are defined as proteinaceous macromolecules located on cell membranes that perform a signal transducing function. Many receptors are located on the outer cell membrane. These cell surface receptors have extracellular and cytoplasmic domains wherein the extracellular domain is capable of specifically binding a substance so that the cytoplasmic domain interacts with another cell molecule as a function of the binding of the substance by the extracellular domain. The substance which is bound by the receptor is called a ligand, a term which is definitionally meaningful only in terms of its counterpart receptor. The term "ligand" does not imply any particular molecular size or other structural or compositional feature other than that the substance in question is capable of binding, cleaving or otherwise interacting with the receptor in such a way that the receptor conveys information about the presence of the ligand to a target molecule. Stated alternatively, not all substances capable of binding a receptor are ligands, but all ligands are capable of binding a receptor. Receptors do not include such substances as immunoglobulins.

Receptors typically are divided structurally into three domains. A highly hydrophobic region of about 20 to 25 residues which is believed to be responsible for embedding the receptor in the cell membrane is flanked on its amino and carboxyl termini by regions that respectively extend into the extracellular and cytoplasmic environment. The extracellular region includes the ligand binding domain. The cytoplasmic region includes a domain for effecting a change in the cytoplasm. Typically, the cytoplasmic region includes an enzymatic function that is activated by receptor aggregation or conformational changes brought on by ligand binding.

Receptors are believed to function by a process variously termed activation or signal transduction. A ligand binds to the extracellular ligand binding domain in such a way that the conformation of the receptor molecule changes within the cytoplasmic region. This conformational change, called activation, modifies the effect of the receptor on cytoplasmic components. Among changes brought about by receptor activation are changes in or development of receptor enzymatic activity.

The pharmaceutical industry in recent years has oriented its research to focus on the role of receptors in disease or injury and to design drugs, generally low molecular weight substances, that are capable of binding to the receptors. Drugs identified in this initial screen are then tested for the desired activity in vivo or in tissue explants. As a result, conventional techniques do not lend themselves to large scale screening. Tissue samples or isolated cells containing the target receptors, e.g. heart atrial tissue, are costly to obtain, present in limited quantity, and difficult to maintain in a functionally viable state. Additionally, it is often difficult to reliably and reproducibly administer the candidate drug to tissue samples. Screening assays using primary explants in tissue culture are undertaken in larger scale than is possible with tissue samples. However, it is more difficult to assay physiological effect and the assays are subject to interference from many sources, e.g. culture media or cultivation conditions. Finally, assays using receptors isolated from natural materials have the disadvantage that the receptor is subject to natural variability and suitable natural sources may not always be available. It is an object herein to provide readily reproducible, simple assay systems that can be practiced on a large scale for determining not only ligand binding but also the character of the binding as agonistic or antagonistic.

Similarly, meaningful clinical diagnoisis often depends upon the assay of biologically active ligand without interference from inactive forms of the ligand, for example, ligands that have been subject to enzymatic or other processes of the test subject that change or even eliminate the activity of the ligand. Immunoassay methods are widely used in determining ligands in test samples. However, it is often quite difficult to identify antibodies that are able to discriminate between the active and inactive forms of a ligand. Receptors have infrequently been used in place of antibodies as analyte binding reagents. However, not all substances that bind to receptors are necessarily capable of inducing receptor activity, i.e. active biologically. It is an object herein to to provide a method that will identify ligands an clinical test samples which are active in inducing or inhibiting signal transduction by their receptors.

Many receptors have been identified that have at least some known in vitro assayable activity that is dependent upon ligand interaction. For example, the binding of EGF to the epidermal growth receptor stimulates a phosphotransferase domain in the receptor to phosphorylate certain target amino acid residues located in its intracellular cytoplasmic domain, a process called autophosphorylation. Receptors also are known to phosphorylate antibodies or specific cytoplasmic substrate polypeptides that bind to the region in which their phosphotransferase active site is located. Unfortunately, other receptors have no known ligand-dependent enzymatic activity, notwithstanding that they are known to bind ligands with high affinity, or their activity is so low that it is difficult to quantitatively assay ligand-dependent activation. It may be desirable for therapeutic purposes to antagonize or agonize a ligand interaction with such cryptic receptors but, in the absence of the tissue concerned or, in some cases an intact organism, no method is available for determining whether a candidate drug is simply binding the receptor in a function-neutral fashion, nor whether the candidate is binding as a agonist or antagonist. Accordingly, it is an object to provide a method for screening candidate drugs for ligand agonist or antagonist activity where the receptor for the ligand exhibits no known signal transduction characteristic.

SUMMARY

These objects are accomplished by the use of a novel receptor hybrid comprising the ligand binding domain of a receptor fused at its C-terminus to the N-terminus of a heterologous reporter polypeptide which is capable of undergoing an assayable change in conformation or function when the ligand binding domain of the receptor binds to either the ligand or to an agonist or antagonist of the ligand.

If a disease or injury is the result of a ligand acting on a given receptor, the objective will be to identify substances capable of counteracting the ligand's effect on the critical receptor, i.e., ligand antagonists. On the other hand, a model therapy for a clinical condition characterized by insufficient ligand activity would consist of drugs that enhance or supplement a defective or absent ligand, i.e., ligand agonists.

The hybrid receptor of this invention is useful in screening methods for identifying receptor-active agonistic drugs. One incubates the hybrid receptor with the candidate drug and assays for the generation of a signal by the heterologous reporter polypeptide. Generally, but not necessarily, the signal generated by the reporter polypeptide is assayed as an activation or stimulation of an enzymatic function of the reporter polypeptide. It is not necessary to include standards having known amounts of ligand unless one wishes to quantify the agonist activity of the candidate; in fact, the ligand which modules the receptor activity in vivo may be completely unknown. It is one of the benefits of this assay system that neither the ligand for the receptor nor the in vivo signal transducing mechanism of the receptors need be known in order to identify agonist drugs.

The hybrid receptor is used to assay amounts of biological ligand in test samples in the same fashion as one screens for agonist drugs. Since this utility, by definition, contemplates a known ligand, then a standard curve using known amounts of ligand is prepared and compared with the test sample results.

Antagonist drug candidates are selected by the same assay as is used for identifying agonists, except that here the hybrid receptor is incubated with a known receptor agonist. The agonist, which may be a drug or the normal in vivo ligand, is incubated with the receptor before or, preferably, simultaneously with contacting the receptor with the candidate drug. Antagonist activity is a function of the displacement of agonist or ligand activity as measured by changes in the reporter polypeptide.

A particular advantage of the hybrid receptor is that it enables a universal, portable assay system for any ligand-receptor interaction. This invention contemplates, for example, that the cytoplasmic domain of a first receptor is selected as the portable reporter polypeptide. This domain is then substituted for the cytoplasmic domain of other receptors in preparing the hybrid receptors of the invention. The assay system, e.g. autophosphorylation assay, useful with the first receptor is then availabe for use with all other hybrid receptors containing the cytoplasmmic domain of the first receptor.

BRIEF DESCRIPTION OF THE FIGURES

FIG. 3a depicts the anti-HER immunoprecipitated autophosphorylation products of mock-transformed controls and recombinant transformant cells. This demonstrates expression of hybrid insulin-EGF receptor constructs in the recombinants.

FIG. 3b demonstrates that the autophosphorylation of the hybrid containing the complete extracellular domain of the insulin receptor is activated by insulin.

FIG. 3c depicts the kinetics of the insulin-activated autophosphorylation of the IER receptor. It shows that the autophosphorylation observed is dependent upon the time of the phosphorylation reaction.

FIG. 3d illustrates the change in SDS-PAGE migration of the IER receptor after insulin activation.

DETAILED DESCRIPTION

Figure 1A:
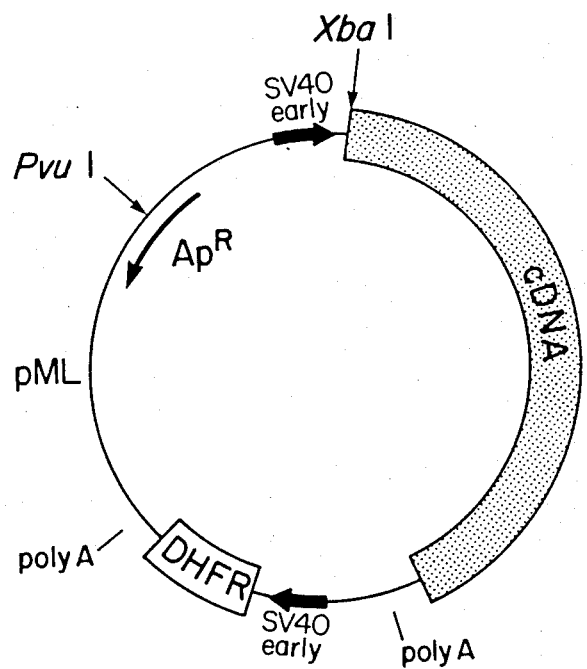
FIG. 1a depicts the composition of a plasmid employed in the expression of hybrids of the insulin and epidermal growth factor receptors. The region coding for different receptor mutants is shown by a shaded bar (cDNA). Early SV40 promoter sequences shown by heavy black arrows and polyA addition sites have been marked. The dihydrofolate reductase (DHFR) coding sequence (Simonsen and Levinson, 1983, "Proc. Natl. Acad. Sci. USA" 80:2495-2499) and restriction sites used for plasmid constructions are shown. Expression of both cDNAs was controlled by promoter sequences of the Simian virus (SV) 40 early region and by 3'- untranslated sequences of the gene coding for the hepatitis B virus surface antigen (Crowley et al., 1983, "Mol. Cell. Biol."3: 44-45). Sequences of the E. coli plasmid pML (a pBR322 derivative suitable for use in mammalian cells; Lusky and Botchan, 1981, "Nature" 293:79) containing the origin of replication and the ampicillin resistance gene were present to allow plasmid replication in E. coli.

The hybrid receptor is the core of the methods described herein. It principally comprises a ligand binding domain and a reporter polypeptide. The ligand binding domain is located within the extracellular region of a receptor. It is often difficult to identify the precise amino acid sequences involved in ligand binding. In fact, several regions may be involved in ligand binding, particularly where the ligand is a polypeptide. Thus, it is preferred that the entire extracellular region of the receptor be assembled into the hybrid. This also will help to ensure that the ligand binding domain is maintained in its proper conformation Suitable ligand binding domains are selected in any one of several ways. First, when one intends to use the hybrid to assay for a known ligand in test samples, or to screen for agonists or antagonists to such ligand, then the ligand binding domain is selected from a known receptor for the ligand. If the ligand is known, but its receptor is not, then it will be necessary to identify its cell surface receptor. This may be accomplished by 1) securing cells from tissues with which the ligand is known to bind or to functionally interact, 2) obtaining from the cells in known fashion a membrane protein preparation, 3) incubating the preparation with the ligand, 4) separating the ligand-receptor complex from the incubation mixture (for example by preinsolubilizing the ligand on cyanogen bromide activated Sepharose), 5) separating the receptor from the ligand, 6) obtaining amino acid sequence from a portion of the receptor, 7) preparing nucleic acid probes encoding the determined amino acid sequence (either a single long probe of >about 40bp or a pool of shorter probes), 8) preparing a cDNA or genomic DNA phage or plasmid (vector) library from the organism or cells from which the receptor was obtained, 9) hybridizing the probes to the library to identify plasmids or phage which contain DNA encoding the receptor, and 10) determining the nucleotide and imputed amino acid sequence of the receptor to the extent necessary to identify the region extending from the amino terminus through a transmembrane sequence. If no single vector contains DNA encoding the entire extracellular domain of the receptor, the desired DNA is assembled by restriction enzyme digestion of the various vectors at common sites, isolation of the appropriate fragments and religation by methods already known per se. Other procedures for identifying receptors for known ligands are known to those skilled in the art or will become available in the future.

A putative receptor may have been identified but its ligand in vivo remains unknown. For example, study of endocrine tissues from such glands as the pituitary or adrenals will lead to the identification of membrane bound proteins that are structurally similar to other known receptors, i.e. they will have a large (typically >500 residues) extracellular domain, a hydrophobic transmembrane sequence and a carboxy-terminal cytoplasmic region. Similarly, a receptor inventory for malignant cells that will be useful for identifying unique receptors present in high density that may be associated with the transformed phenotype. The extracellular domains of such receptors are also useful herein.

A receptor and its ligand may have been identified but the cytoplasmic domain may have no known function, e.g. it is not known to have phosphotransferase activity, to activate adenylate or guanylate cyclase, or to transport liqand. The ligand binding domain from such receptors is useful notwithstanding that the ligand-receptor interaction produces no or insufficiently detectable signal in the native receptor because a detectable signal is provided by the reporter polypeptide in the hybrid construction. Thus, in the absence of the reporter polypeptide no method would be available to determine in the case of some receptor whether a receptor-bound candidate drug was binding nonspecifically or was acting as an agonist or antagonist, nor would it be possible to assay for biologically active native ligands.

The reporter polypeptide is heterologous to the ligand binding domain and is any polypeptide that changes its character upon the binding of a ligand to the binding domain. This change in character is generally detected by a change in the enzymatic activity or immunological identity of the reporter polypeptide. Generally the reporter polypeptide will be the cytoplasmic domain of a heterologous receptor or receptor analogue, e.g. oncogene, which is known to undergo a change in immunological or enzymatic identify upon ligand binding. It is preferred to use the cytoplasmic phosphotransferase from such receptors as the insulin or epidermal growth factor receptors. However, other receptors as the B-adrenergic receptor, acetylcholine receptor, adrenaline receptor and the like are known to bind proteins termed G proteins that serve as intermediate transducing molecules in the activation or inhibition of adenylate or guanylate cyclases. Such proteins have been isolated and characterized. It is within the scope herein to use as the reporter polypeptide the G protein binding domains of such receptors. It is not necessary to use the entire cytoplasmic domain from a heterologous receptor or receptor analogue, only that portion that performs the desired function herein, nor is it necessary to use a heterologous cytoplasmic domain that is an intact, unmodified sequence from another receptor. For example, an amino acid sequence variant or derivative of the cytoplasmic domain of the receptor supplying the ligand binding domain is also acceptable.

Without being limited to a particular theory of function, we believe that the change in the character of the reporter polypeptide is not caused by steric hinderance of the reporter by the ligand, e.g. where the ligand occludes an active site on the reporter domain by virtue of steric bulk. Rather, the method herein harnesses the signal transducing mechanism of receptors wherein changes in the ligand binding domain are transduced through the receptor molecule to the reporter domain by conformational changes in the molecule, which changes affect the function or character of the cytoplasmic domain of the reporter. We have discovered that this transducing mechanism also functions when the reporter polypeptide is heterologous to the ligand binding domain.

Optionally, the hybrid receptor will contain a transmembrane sequence fused between the ligand binding domain and the reporter polypeptide. Typical transmembrane domains contain about from 20 to 25 residues and show a hydropathy peak of about from 1.5 to 3.5. They contain a high proportion of residues having hydrophobic side chains, e.g. leucine, isoleucine, phenylalanine, valine and methionine. Suitable transmembrane sequences are obtained from the receptor supplying the extracellular ligand binding domain, although the transmembrane sequence also may be entirely synthetic or obtained from integral membrane proteins or unrelated receptors, in the last instance including the transmembrane region ordinarily associated with the reporter polypeptide where the reporter is the cytoplasmic domain of a heterologous receptor.

The hybrid receptor components suitably originate from humans, animals, plants, insects, microorganisms including parasites, viruses and fungi and other suitable species. The species of origin for the ligand binding domain is selected for the presence of a receptor capable of binding the ligand of interest or for the presence of the target physiological activity. It is not necessary that the reporter polypeptide or transmembrane region be from the same species as the ligand binding domain.

The hybrid receptors preferably are synthesized in recombinant cell culture because they are generally too large and complex to practically synthesize by in vitro methods that are available to the art today.

Recombinant methods for synthesis of the hybrid receptor commence with the construction of a replicable vector containing nucleic acid that encodes the hybrid receptor. Vectors typically perform two functions in collaboration with compatible host cells. One function is to facilitate the cloning of the nucleic acid that encodes the hybrid receptor, i.e., to produce usable quantities of the nucleic acid. The other function is to direct the expression of the hybrid receptor. One or both of these functions are performed by the vector-host system. The vectors will contain different components depending upon the function they are to perform as well as the host cell that is selected.

Each vector will contain nucleic acid that encodes the hybrid receptor. Typically, this will be DNA that encodes the hybrid receptor in its mature form linked at its amino terminus to a secretion signal. This secretion signal preferably is the signal presequence that normally directs the secretion of the receptor from which the ligand binding domain was obtained. However, suitable secretion signals also include signals from other receptors or from secreted polypeptides of the same or related species.

The secreted hybrid will lodge in the recombinant host membrane if it contains a transmembrane region. On the other hand, if such a region is not present in the hybrid, then the hybrid may be secreted into the culture medium. Ordinarily, hybrids are preferred that contain a transmembrane region so as to retain as much structural fidelity as possible. However, the purification of transmembrane-deleted receptors is less complex than in the case of membrane-bound because in the latter instance the hybrid receptor should be purified free of other cell membrane proteins. Furthermore, the cell-bound hybrid receptor may exert an undesired biological effect on the host if induced to accumulate in large populations in the cell membrane during the growth phase. This potential problem is overcome by placing the nucleic acid encoding the hybrid receptor under the control of an inducible promoter.

In cloning vectors, the hybrid receptor-encoding nucleic acid ordinarily is present together with a nucleic acid sequence that enables the vector to replicate in a selected host cell independent of the host chromosomes. This sequence is generally an origin of replication or an autonomously replicating sequence. Such sequences are well-known for a variety of bacteria, yeast and higher eukaryotic cells. The origin from the well-known plasmid pBR322 is suitable for E. coli bacteria, the $2\mu$ plasmid origin for yeast and various viral origins for mammalian cells (SV40, polyoma, adenovirus or bovine papilloma virus). Less desirably, DNA is cloned by insertion into the genome of a host. This is readily accomplished with bacillus, species, for example, by inserting into the vector DNMA that is complementary to bacillus genomic DNA. Transfection of bacillus with this vector results in homologous recombination with the genome and insertion of the hybrid receptor DNA. However, the recovery of genomic DNA encoding the hybrid receptor is more complex than obtaining exogenously replicated viror or plasmid DNA because restriction enzyme digestion is required to recover the hybrid receptor DNA from the genome of the clonging vehicle.

Expression and cloning vectors should contain a selection gene, also termed a selectable marker. This is a gene that encodes a protein necessary for the survival or growth of a host cell transformed with the vector. The presence of this gene ensures the growth of only those host cells which express the inserts. Typical selection genes encode proteins that (a) confer resistance to antibiotics or other toxins, e.g. ampicillin, neomycin, methotrexate or tetracycline, (b) complement auxotrophic deficiencies, or (c) supply critical nutrients not available from complex media, e.g. the gene encoding D-alanine racemase for bacilli.

A suitable selection gene for use in yeast is the trpl gene present in the yeast plasmid YRp7 (Stinchcomb et al., 1979, "Nature", 282: 39; Kingsman et al., 1979, "Gene", 7: 141; or Tschemper et al., 1980, "Gene", 10: 157). The trpl gene provides a selection marker for a mutant strain of yeast lacking the ability to grow in the absence of tryptophan, for example ATCC No. 44076 or PEP4l (Jones, 1977, "Genetics", 85: 12). The presence of the trpl lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Examples of suitable selectable markers for mammalian cells are dihydrofolate reductase (DHFR), thymidine kinase or proteins for neomycin resistance. Such markers enable the identification of cells which were competent to take up the hybrid receptor nucleic acid. The mammalian cell transformants are placed under selection pressure which only the transformants are uniquely adapted to survive by virtue of having taken up the marker. Selection pressure is imposed by culturing the transformants in successive rounds of cells culture in which the concentration of selection agent in the medium is successively increased, thereby leading to amplification of both the selection gene and the DNA encoding the hybrid receptor. Increased quantities of hybrid receptor are synthesized from the amplified DNA.

For example, selection for DHFR transformed cells is conducted in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, 1980, "Proc. Nat'l. Acad, Sci. USA" 77: 4216.

A particularly useful DHFR is a mutant DHFR that is highly resistant to methotrexate (MTX) (EP 117,060A). This selection agent can be used with any otherwise suitable host, notwithstanding the presence of endogenous DHFR. One simply includes sufficient MTX in the medium to inactivate all of the endogenous DHFR, whereupon MTX selection becomes solely a function of amplification of the mutant DHFR DNA. Most eukaryotic cells which are capable of adsorbing MTX appear to be methotrexate sensitive. One such useful cell line is a CHO line, CHO-K1 (ATCC No. CCL 61).

Other methods, vectors and host cells suitable for adaptation to the synthesis of the hybrid receptor in recombinant vertebrate cell culture are described in M. J. Gething et al., "Nature" 293: 620–625 (1981); N.

Mantei et al., "Nature" 281: 40–46; and A. Levinson et al., EP 117,060A and 117,058A.

Expression vectors, unlike cloning vectors, should contain a promoter and/or other sequence which is recognized by the host organism for strong transcription of the hybrid receptorencoding DNA. This is generally a promoter homologous to the intended host. In the case of vectors for higher eukaryotes, enhancer sequences are useful for further increasing transcription from promoters. Unlike promoters, enhancers do not need to be located 5' to the hybrid receptor encoding nucleic acid. Commonly used promoters for prokaryotes include the β-lactamase and lactose promoter systems (Chang et al., 1978, "Nature", 275: 615; and Goeddel et al., 1979, "Nature", 281; 544), alkaline phosphatase, a tryptophan (trp) promoter system (Goeddel 1980, "Nucleic Acids Res." 8: 4057 and EPO Appln. Publ. No. 36,776) and hybrid promoters such as the tac promoter (H. de Boer et al., 1983, "Proc. Nat'l. Acad. Sci. USA" 80: 21-25). However, other known microbial promoters are suitable. Their nucleotide sequences have been published, thereby enabling a skilled worker operably to ligate them to DNA encoding the hybrid receptor in plasmid vectors (Siebenlist et al., 1980, "Cell" 20: 269) using linkers or adaptors to supply any required restriction sites. Promoters for use in prokaryotic systems also will contain a Shine-Dalgarno (S.D.) sequence operably linked to the DNA encoding the hybrid receptor.

Suitable promoting sequences in yeast vectors include the promoters for metallothionein, 3-phosphoglycerate kinase (-Hitzeman et al., 1980, "J. Biol. Chem.", 255: 2073) or other glycolytic enzymes (Hess et al., 1968, "J. Adv. Enzyme Reg.", 7: 149; and Holland, 1978, "Biochemistry", 17: 4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceralidehyde-3-phosphate dehydrogenase, as well as enzymes responsible for maltose and galactose utilization. Suitable vectors and promoters for use in yeast expression are further described in R. Hitzeman et al., EP 73,657A.

Transcription from vectors in mammalian host cells is controlled by promoters and/or enhancers obtained from the genomes of bovine papilloma virus, vaccinia virus, polyoma virus, adenovirus 2, retroviruses, hepatitus-B virus and most preferably Simian Virus 40 (SV40), operably linked to the hybrid receptor nucleic acid. The early and late promoters of the SV40 virus are as conveniently obtained as an SV40 restriction fragment which also contains the SV40 viral origin of replication (Fiers et al., 1978, "Nature", 273: 113). Of course, promoters or enhancers from the host cell or related species also are useful herein.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably lined means that the DNA sequences being linked are contiguous and, in the case of secretory leader, contiguous and in reading frame.

Expression vectors used in eukaryotic host cells (yeast, fungi, insect, plant, animal or human) will also contain sequences necessary for the termination of transcription and for stabilizing the mRNA. Such sequences are commonly available from the 3' untranslated regions of eukaryotic or viral cDNAs. These regions contain regions that are transcribed as polyadenylated segments in the untranslated portion of the mRNA encoding the hybrid receptor. The 3' untranslated regions also include transcription termination sites.

Suitable host cells for cloning or expressing the vectors herein are prokaryotes, yeast or higher eukaryotic cells. Prokaryotes include gram negative or gram positive organisms, for example E. coli or bacilli. A preferred cloning host is E. coli 294 (ATCC 31,446) although other gram negative or gram positive prokaryotes such as E. coli B, E. coli X1776 (ATCC 31,537), E. coli W3110 (ATCC 27,325), pseudomonas species, or Serratia Marcesans are suitable.

In addition to prokaryotes, eukaryotic microbes such as filamentous fungi or yeast are suitable hosts for the hybrid receptor encoding vectors. Saccharomyces cerevisiae, or common baker's yeast, is the most commonly used among lower eukaryotic host microorganisms. However, a number of other genera, species and strains are commonly available and useful herein.

The preferred host cells for the expression of functional hybrid receptors are cultures of cells derived from multicellular organisms. In many cases, hybrid receptors contain hydrophobic regions that are incompatible with lower microorganisms, require complex processing to properly form disulfide bonds and often require subunit processing. In addition, it is desirable to glycosylate the receptors in a fashion similar to the native receptors. All of these functions can be best performed by higher eukaryotic cells. In principle, any higher eukaryotic cell culture is workable, whether from vertebrate or invertebrate culture, although cells from mammals such as humans are preferred. Propagation of such cells in culture is per se well known. See Tissue Culture, Academic Press, Kruse and Patterson, editors (1973). Examples of useful mammalian host cell lines are VERO and HeLa cells, Chinese hamster ovary cell lines, and WI38, BHK, COS-7 and MDCK cell lines.

The hybrid receptors of this invention are employed in drug screening or biologically active ligand assay by a process that fundamentally comprises incubating the receptor with the test sample, controls and (optionally) standards, followed by measuring change in the reporter polypeptide. Since we have discovered that ligand binding causes a change in the conformation of the reporter polypeptide it is within the scope hereof to detect such changes by any one of several methods. Typically, one measures changes in the protein binding or enzymatic activity of the reporter polypeptide. In one embodiment an antibody is raised against the activated conformation and the binding of this antibody to the hybrid receptor is measured after the receptor has been incubated with the ligand or candidate drug. This assy is conducted in the same fashion as conventional immunoassay methods for any protein antigen. Antibodies are known per se that are capable of binding phosphotyrosien containing proteins (Wang, 1985, "Mol. and Cell. Biol" 5(12): 3640–3643; Ross et al., 1981, "Nature" 294: 654; and Pang et al., 1985, "Arch. Biochem. Biophys." 242(1): 176). While those antibodies are useful in the method herein, hybrid receptors enable the selection of antiphosphotyrosine antibodies that, unlike the prior art antibodies, are specific for the reporter polypeptide and will not cross-react with other receptors or phosphorylated proteins, yet which are just as versatile in measuring the effect of a ligand on a receptor binding domain. The disadvantage of this method is that it requires a phase separation to remove the unbound labelled antibody from the reporter-bound antibody. However, the method does not require covalent modification of the hybrid receptor.

Analogous to assays using the binding of a specific antibody to the reporter polypeptide are methods that directly or indirectly measure the binding to the reporter of a non-immune binding protein with which it normally interacts. Typical binding proteins are the G proteins that associate with certain ligandactivated receptors. The reporter polypeptide in this case is the cytoplasmic domain of a receptor such as the beta-adrenergic receptor. The binding of the G protein is assayed in the same fashion as antibody binding, e.g. by displacement of labelled G protein, or by determination of GTP or ATP binding to the activated G protein.

If the reporter polypeptide is the enzymatically active cytoplasmic domain of a heterologous receptor, then the preferred detection method will be an assay for that activity. At the present time such activity includes protein phosphorylkinase activity, primarily tyrosine kinase activity but in some cases serine or threonine kinase activity. Kinase activity is measurable in any way in which kinase activity has been assayed heretofore. One conventional, and presently preferred, method for kinase activity is to assay the incorporation of radiophosphorus into the reporter polypeptide through autophosphorylation with $^{32}P$. It is preferred to form hybrids of receptors having the same class of activity.

However, it is within the scope herein to measure changes in the reporter polypeptide by methods other than enzymological activity or polypeptide interactions. One such method contemplates binding an organic moiety to the receptor that undergoes a change in character upon ligand binding. For example, the reporter polypeptide is labelled with a stable free radical, a chemiluminescent group or a fluorescent molecule such as fluorescein isothiocyanate. Each of these labels are well known in the diagnostic immunochemistry art and conventional methods are well known for covalently linking them to proteins. These methods are useful for labelling the reporter polypeptide in the same fashion as other proteins. Changes in the conformation of the receptor polypeptide upon the binding of ligand or active candidate drug to the ligand binding domain are detected by changes in the label. For example, the rotational moment of a stable free radical label will be increased or decreased by ligand-activated changes in reporter polypeptide conformation. Similarly, the fluorescence or luminescence of reporter polypeptide labels will change upon the binding of ligand or active candidate to the receptor because of the reorientation of polypeptide species that engage in intramolecular energy transfers. This is detected by changes in the intensity, polarization or wave length of the label molecule; typically, one detects the enhancement or quenching of the label fluorescence or chemiluminescence. The advantage of the labelled reporter method is that the ligand or candidate drug assay is conducted exclusively in aqueous solution and no phase separation is required. This permits the automation of the screening method using continuous flow instruments such as Autoanalyzers. Such methods are useful with native as well as the hybrid receptors.

In order to simplify the Examples certain frequently occurring methods will be referenced by shorthand phrases.

"Plasmids" are designated by a low case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" or "cleavage" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained and then a number designating the particular enzyme. Appropriate buffers and substrate amounts for particular restriction enzymes are specified by the manufacturer. Incubation times of about 1 to several hours at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5'phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular CLoning* pp. 133–134).

"Filling" or "blunting" refers to the procedure by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2-15 $\mu$g of the target DNA in 10 mM Mg Cl$_2$, 1 mM dithiothreitol, 50 mM NaCl, 10 mM Tris (pH 7.5) buffer at about 37° C. in the presence of 8 units of the Klenow fragment of DNA polymerase I and 250 $\mu$M of each of the four deoxynucleoside triphosphates. The incubation generally is terminated after 30 min. by phenol and chloroform extraction and ethanol precipitation.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the DNA from the gel. This procedure is known generally. For example, see R. Lawn et al., 1981, "Nucleic Acids Res." 9:6103–6114, and D. Goeddel et al., 1980, "Nucleic Acids Res.: 8:4057.

"Transformation" means introducing DNA into an organism so that the DNA is replicable, either as an extrachromosomal element or chromosomal integrant. Unless otherwise provided, the method used herein for transformation of E. coli is the $CaCl_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 1 μg of the DNA fragments to be ligated.

"Preparation" of DNA from transformers means isolating plasmid DNA from microbial culture. Unless otherwise provided, the alkaline/SDS method of Maniatis et al., Id., P. 90, may be used.

"Oligonucleotides" are short length single or double stranded polydeoxynucleotides which are chemically synthesized by known methods and then purified on polyacrylamide gels.

The following examples are intended to merely illustrate the best mode now known for practicing the invention, but the invention is not to be considered limited thereto.

All literature citations herein are expressly incorporated by reference.

EXAMPLE 1

Construction of the Insulin Receptor (IR) Expression Plasmid

A gel purified SalI fragment (5.2 kb) from λHIR-P12 containing the entire HIR coding sequence was subcloned into the pUC12 (New England Biolabs) polylinker region by digesting pUC12 with SalI and ligating the purified SalI fragment to the vector. Colonies were grown up and screened for clones having the desired orientation with the 5′ end of the HIR coding sequence next to the pUC12 XbaI site. This vector was cut with XbaI and DraI (DraI is located in the 3′ untranslated region of HIR) and the HIRcontaining fragment was isolated. This fregment was inserted into a mammalian expression vector (pCVSVEHBVE400, European Publn. No. 117,060), which had been digested first with BamHI. The BamHI cohesive terminii were filled and the plasmid then was digested with XbaI. Thus, insertion of the XbaI-DraI was only possible in the orientation necessary for expression of the HIR mRNA. The resulting insulin receptor expression plasmid was designated pCVSV-HIRc.

EXAMPLE 2

Construction of a Vector for Expressoin of an Insulin-EGF Receptor Hybrid

The following fragments were ligated in a four-factor ligation: (a) A 931 bp BamHI-AatII restriction fragment from the IR expression plasmid pCVSVE-HIRc, (b) a 1150 bp ApaI-SstI restriction fragment of the human EGF receptor sequence contained in the recombinant phage γHER-A64 (Ullrich et al., 1984, "Nature"309: 418-425), (c) a synthetic oligonucleotide linker containing 5′-CCCGTCAAATATCGCCACTG-GGATGGTGGGGGCC-3′ and 5′ -CCCACCATC-CCAGTGGC GATATTTGACGGGACGT-3′, and (d) pUC12 opened with SstI and BamHI. In this way sequences coding for the extracellular domain of the insulin receptor were joined to sequence coding for the transmembrane and cytoplasmic domains of the EGF receptor and placed into an expression plasmid. Plasmid pUC12/HIR-HER Int. which contained DNA encoding the hybrid was recovered from an ampicillin resistant colony of transformant E. coli 294. This plasmid was digested with BamHI and ApaI and a 965 bp fragment containing the IER junction was recovered (fragment 1). pCVSVHIRc was digested with PvuI and BamHI and a 3117 bp fragment containing the rest of the IR coding sequence and parts of the mammalian expression vector was recovered (fragment 2). γHER-A64 is digested with ApaI-BglII and an 810 bp fragment recovered (fragment 3) and with BglII-XmnI and a 1 kb fragment recovered (fragment 4). Fragments 3 and 4 code for the transmembrane and cytoplasmic domains of the human EGF receptor. pCVSVEHBVE400 is digested with BamHI, the restriction site was enfilled and the DNA subsequently digested with PvuI. A 4 kb BamHI-PvuI fragment was recovered (fragment 5) coding for parts of the mammalian expression vector as described. A mixture of fragments 1, 2, 3, 4 and 5 was ligated and used to transform E. coli 294 DNA. Ampicillin resistant colonies were screened by restriction analysis. A 240 bp PstI fragment overlapping the HIR-HER junction was cloned into M13Ty131 and sequenced to verify the expected junction.

An expression vector for a hybrid receptor not containing a transmembrane region is constructed in the same fashion as described above using pCVSV-HIRc except that the transmembrane region downstream from the ApaI EGF receptor is deleted by M13 mutagenesis and an in-frame ApaI adaptor ligated to the deleted ER fragment.

A vector encoding the hybrid receptor IαER, a hybrid of the insulin receptor α chain with the EGF receptor transmembrane and cytoplasmic domains without any HIR B-chain sequence, was made by oligonucleotide-directed deletion mutagenesis of the IER plasmid. A 2.1 kb BglII restriction fragment coding for joined insulin and EGF receptor sequences was introduced into the BamHI site of an M13mp10 vector. Molecules with the desired orientation of the IR sequences next to the HindIIi site of M13mp10 were identified and a single-stranded template was prepared for deletion mutagenesis with the oligonucleotide 5′CCCCAGG-CCATCTATCGCCACTGGGA-3′based on the protocols of Adelman et at. "DNA" 2: 183–193 (1983). 50 ng of phosphorlyated primer was hybridized to 2 μg of single-stranded M13 template. The mutagenized second strand was completed and double-stranded molecules were introduced into E. coli JM101. Resulting plaques were screened as described by Benton and Davis "Science" 196: 180–182 (1977) at high stringency using the primer as a hybridization probe. Double-stranded DNA was prepared and a 1.2 kb BstEII restriction fragment containing the mutated region was used to replace the respective DNA fragment in the IER expression plasmid, yielding PIαER.

EXAMPLE 3

Expression of the Hybrid Insulin and EGF Receptors

COS-7 monkey kidney cells (Gluzman, 1981, "Cell" 23: 175–182) were cultured in DMEM mixed with F12 medium (50:50), containing 10 percent fetal bovine serum and antibiotics. All cell culture media (Gibco) contained 2 mM L-glutamine and 20 mM HEPES pH 7.4.

pIER or pIαER from Example 2 was introduced into COS-7 cells by calcium phosphate coprecipitation based on the protocol of Graham and Van der Eb, 1973, "Virology" 52: 456–467. Subconfluent cells were transfected with 10 μg of plasmid DNA per 8 cm culture dish. Plasmid DNA was dissolved in 0.55 ml of 1 mM Tris pH 7.5, 0.1 mM EDTA, 250 mM CaCl$_2$, after which 0.5 ml of 50 mM HEPES pH 7.12, 280 mM NaCl and 1.5 mM Na$_2$HPO$_4$ was slowly added. A precipitate gradually formed within 45 min. which was added to the cell culture medium. The transfected COS-7 cells were cultured for 53 hrs. at 37° C. in DMEM mixed with F-12 medium (50:50) containing antibiotics, 2 mM L-glutamine, 20 mM HEPES and 10% by volume fetal bovine serum (pH 7.4).

Figure 2:
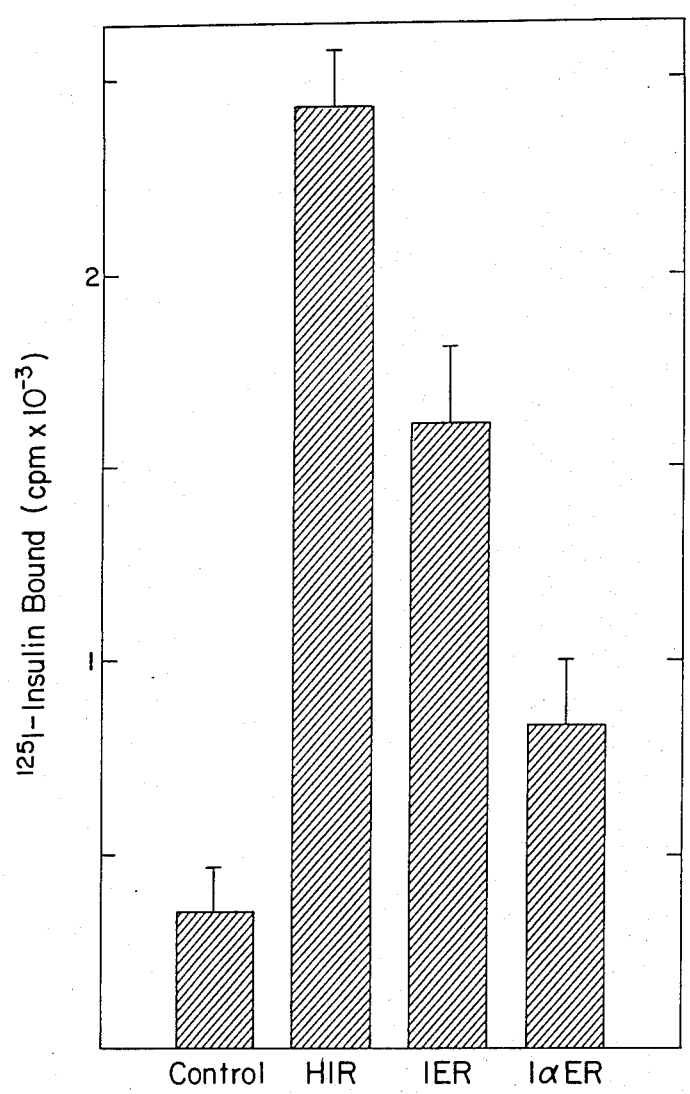
FIG. 2 illustrates that $^{125}I$ insulin binding to COS-7 cells increases when the COS-7 cells are transfected with the cDNA constructs of FIG. 1a, compared to cells transfected with a control expression vector.

COS-7 cells tranformed with pIER or pIαER were washed two times with PBS and incubated in 1 ml of serum-free cell culture medium per 2.2 cm well containing 0.2% bovine serum albumin (Sigma), bacitracin (0.5 mg/ml, Sigma) and $^{125}$I insulin (0.5 μCi/well) at 93 μCi/μg for 2 h at 21° C. Cells were washed 3 times with PBS at 4° C. and lysed in 0.5 ml 0.1 percent SDS, 0.1 M NaOH for 30 min. at 37° C. The radioactivity was determined in a gamma counter. FIG. 2 demonstrated that insulin binding to the transformants increased over that of controls.

Human epidermoid carcinoma cells A431 (a source of EGF receptor controls) were cultured in DMEM containing 4.5 mg glucose per liter, 10 percent fetal bovine serum and antibiotics.

EXAMPLE 4

Hormone Stimulated Autophosphorylation of Normal and Hybrid Receptors pIER or pIαER transformed and mock transformed COS-7 cell monolayers grown in 8 cm culture dishes for 53 hours, or A431 cells, were washed twice with PBS and solubilized as described by Kris et al., 1985, "Cell" 40: 619–625. One ml of 50 mM HEPES buffer pH 7.5 containing 150 mM NaCl, 1.5 mM MgCl$_2$, 1 mM EGTA, 10 percent glycerol, 1 percent Triton X-100, 1 percent Aprotinin (Sigma) and 4 μg/ml phenylmethylsulfonyl fluoride (PMSF) (Sigma) and 0.5 mg/ml bacitracin (Sigma) was added to the monolayers at 4° C. for 5 min. The buffer which contained the solubilized cellular proteins was removed from the culture dish and centrifuged at 10,000 g for 5 min at 4° C. Culture supernatants from transmembrane-deleted hybrid receptor transformed cells are centrifuged at 10,000 g for 5 min. at 4° C. 0.2 ml of the cell lysis or culture supernatant was incubated with 200 nM insulin (Sigma) or 1 μM EGF for 1 hour.

A mouse monoclonal antibody capable of binding the insulin receptor (CII25.3, described by Ganguly et al., 1985, "Current Topics in Cellular Regulation" 27: 83–94) was insolubilized by adsorption to protein A-Sepharose. However, it will be appreciated that any polyclonal or monoclonal anti-insulin receptor antibody can be used. 1 μl of antibody was mixed with 50 μl of a swollen and prewashed 1:1 protein A-Sepharose slurry in detergent-free lysis buffer for 30 min in order to adsorb the anti-IR antibody.

Figure 1B:
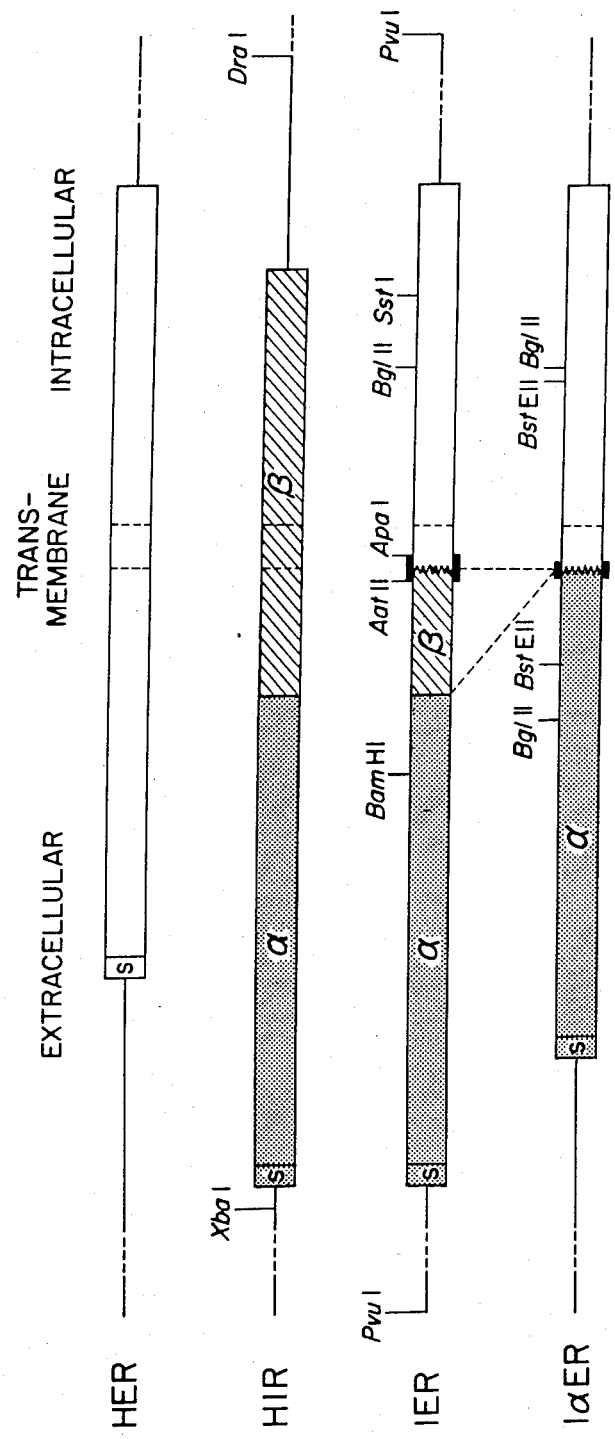
FIG. 1b is a schematic comparison of insulin (HIR) and EGF (HER) receptors and a hybrid receptors IER adn IαER prepared therefrom. Human EGF receptor (HER), human insulin receptor (HIR), insulin-EGF receptor chimera (IER), and insulin-α-subunitEGF receptor chimera (IαER) cDNAs are represented by horizontal lines and coding sequences shown as a dotted box for HIRα sequences (α), as a shaded box for HIRβ, and as an open box for HER sequences. The coding regions have been aligned at the transmembrane domain (not shown in scale). The coding segment for the protein signal sequence is marked by (S) and the precursor cleavage sites are indicated by a vertical line. The junction of the heterologous receptor cDNAs is shown by a zigzag line and synthetic oligonucleotides used at the junctions are represented by black bars. DNA restriction endonuclease cleavage sites relevant for the constructions are marked on top of the cDNA sequences.

50 μl of insolubilized anti-IR antibody slurry was added to the EGF or insulin treated cell lysate or cell culture supernatant and incubated for 15 min. at 4° C. The resulting immunoprecipitate was washed 4 times with 0.9 ml HNTG buffer (20 mM HEPES pH 7.5, 150 mM NaCl, 10 percent glycerol, and 0.1 percent Triton X-100). The precipitate in a volume of 30 μl was adjusted to 5 mM MnCl$_2$, and 15 μCi of γ-$^{32}$P-ATP (5,000 Ci/mmol) was added for 0.5-10 min. at 4° C. The final ATP concentration was 0.1 pM ATP (for EGF, IER or IαER transformants and their controls) or 100 μM ATP (for HIR transformants and their controls). The autophosphorylation reaction was stopped by adding 20 μl of 3 times concentrated SDS sample buffer. The autophosphorylation reaction was terminated after 5 min. in FIG. 3a and 3d, 1 min. in FIG. 3b and after the times indicated in FIG. 3c by boiling for 5 min. The samples were centrifuged were and 20 μl aliquots analyzed on 5 percent/7 percent SDS polyacrylamide gels (Laemmli, 1970, "Nature" 277: 680–685)

Figure 3:
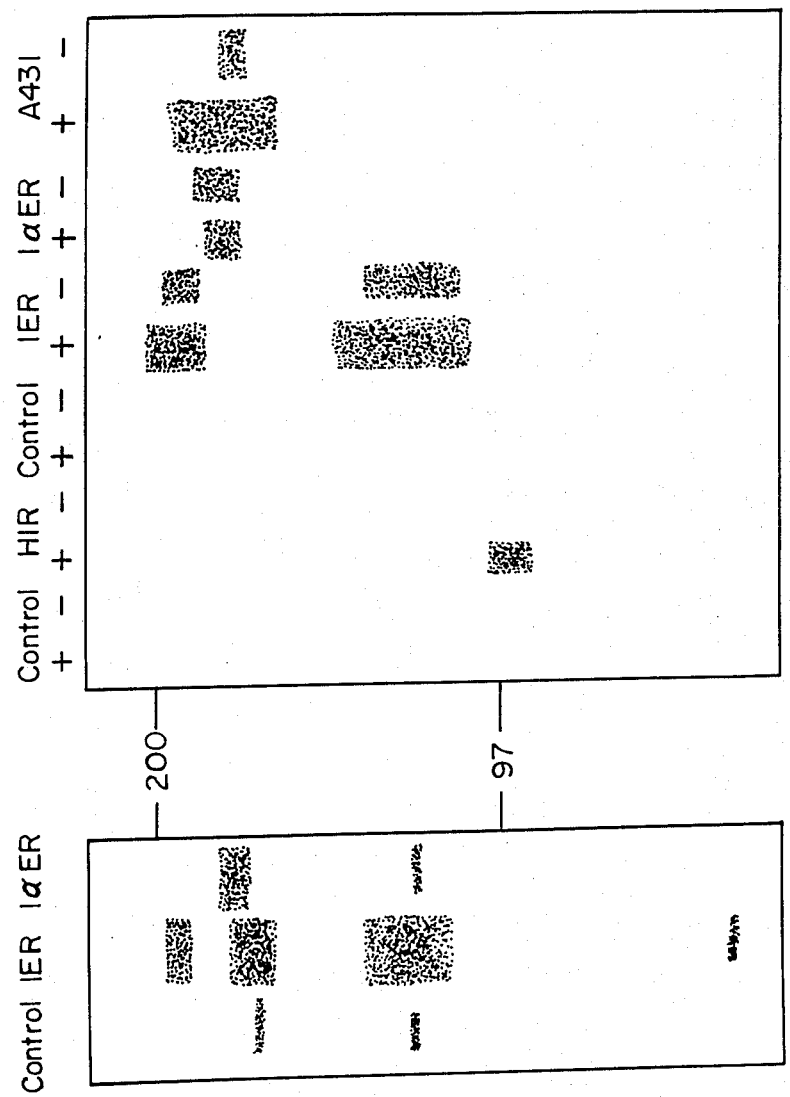
FIGS. 3a-3d are SDS PAGE reducing electrophoresis gels of autophosphorylated detergent lysates obtained from various transformed and control cells and immunoprecipitated with appropriate antibodies as noted in the Example. The (+) and (−) gels represent insulin or (in the case of A431) EGF-treated receptors. Numbers in the margins are marker molecular weights.

The patterns obtained on SDS-PAGE reducing gels matched the $^{35}$S-Met labeling result for those polypeptides that contain tyrosine kinase sequences. FIG. 3b (HIR+) shows the insulinstimulated autophosphorylation of the human insulin receptor β subunit above the endogenous COS-7 control. In this case the insulin induction effect is strong, although the visualized signal is weak due to the ATP concentration (100 μM) required by the insulin receptor kinase. In contrast, only picolmolar concentrations are needed to measure EGF receptor kinase activity and EGF stimulation, as shown in the A431 cell EGF receptor control (A431). The characteristics of the chimeric receptor molecule IER reflects the presence of the EGF receptor kinase because of the low ATP concentrations required. Since ligand induction increases the Vmax of the kinase, maximal induction (4 fold) is observed in a 30 second reaction at 4° C. (FIG. 3c). This finding is in good correlation with the kinetic properties of the wild type EGF receptor (Staros et al., 1985, in *Molecular Aspects of Cellular Regulation Vol. 4: Molecular Mechanisms of Transmembrane Signaling*) and indicates that the EGF receptor kinase retains its original characteristics when controlled by the insulin binding domain.

Surprisingly, the insulin-stimulated and unstimulated 130 kd phosphoprotein subunits of the IE receptor hybrid display a subtle but reproducible size difference (FIG. 3d). This observation raises the possibility that ligand-indiced enzymatic activity leads to phosphorylation of tyrosine residues not modified at basal levels; a subsequent conformational change of the cytoplasmic receptor domain could alter migration characteristics in SDS gels. A similar change may occur in the intact EGF receptor but has not been detected due to the larger size of the monomeric 170 kd glycoprotein. Electrophoretic migration changes have been reported for other autophosphorylated proteins such as Ca$^{2+}$/Calmodulin-dependent protein kinase (Kuret et al., 1985, "J. Biol. Chem." 260:6427–6433), type II cAMP-dependent protein kinase (Hemmings et al., 1981, "Eur. J. Biochem." 119:443–451).

Since uncleaved chimeric proreceptor IER displays insulinstimulated autophosphorylation (FIG. 3b and 3c, IER+gel, top band), the tertiary structure necessary for insulin binding and signal transduction must be formed prior to insulin receptor preteolytic processing, consistent with previous reports (Blackshear et al., 1983, "FEBS" 158:243-246; Rees-Jones et al., 1983, "Biochem. Biophys. Res. Comm." 116:417-422). Our experiments with the chimeric construct IαER, in which the extracellular portion of the insulin receptor $\beta$ subunit and the proreceptor cleavage site are deleted, (FIG. 3b, IαER compare+and−) indicate that despite the apparent ability of the resulting 180 kd single-chain glycoprotein to bind insulin, insulin activation of the cytoplasmic kinase domain is lost.

As shown above, insulin regulates the rate of the EGF receptor autophorylation activity at subpicomolar concentrations of ATP, conditions under which the phosphotransferase of the insulin receptor is inactive. Hormone control was only observed for the hybrid IER containing the complete extracellular portion of the insulin receptor, including the signal for receptor processing into the $\alpha$ and $\beta$ subunits and the amino terminus of the $\beta$ subunit. The receptor appears to be processed in our expression system. In the case of the chimera IαER lacking any portions of the $\beta$ subunit and consequently the cleavage signal, no hormone effect was observed. We conclude that this structural difference between IER and IαER has a profound effect on the structure of the chimeric receptor that is crucial for signal transduction.

EXAMPLE 5

Construction of a Vector Encoding a Receptor-Oncogene Hybrid (HER-erbB)

Figure 4:
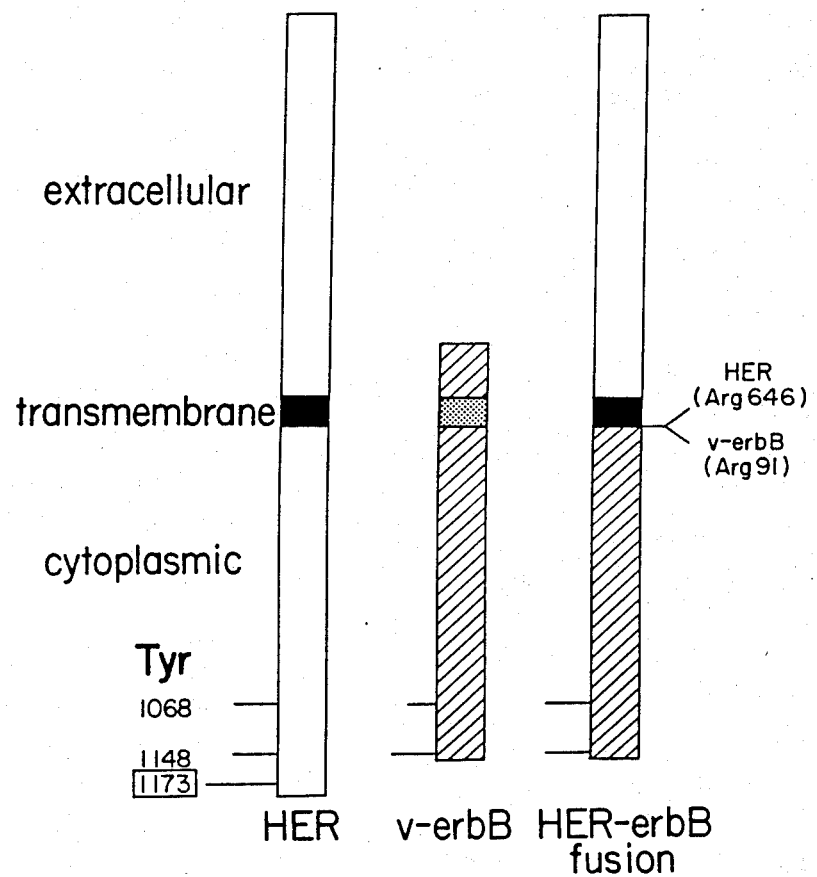
FIG. 4 depicts the structure of HER-erbB, a hybrid receptor containing the epidermal growth factor extracellular domain and a fragment of the erbB oncogene to serve as the reporter molecule.
Figure 5:
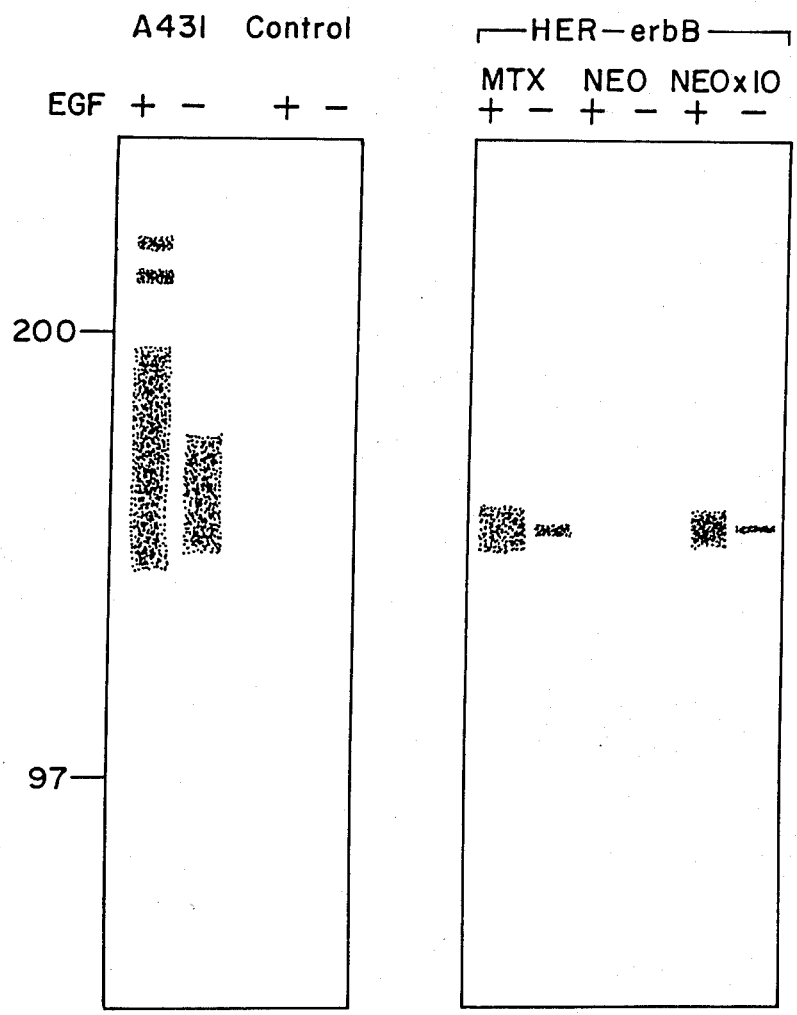
FIG. 5 depicts electrophoresis gels demonstrating autophosphorylation of a hybrid oncogene-receptor construct in the presence (+) or absence of ligand (EGF)(−).

We constructed a hybrid receptor comprised of the intracellular domain of the v-erbB oncogene product fused to the extracellular and transmembrane domains of the EGF receptor (HER-erbB; FIG. 4).

The hybrid receptor is expressed from a plasmid under the control of the early promoter of SV40. This plasmid also contains a mutant DHFR gene for methotrexate (MTX) resistance. Selection is accomplished by cotransformation with a plasmid encoding a neomycin resistance gene and the DNA amplified by selection a MTX-containing culture media.

γHER-A64 (Ullrich et al.) was digested with SacI and NarI and a restriction fragment coding for the complete extracellular and transmembrane domain of the EGF receptor was recovered. A 1.7 kb AhaII-StuI restriction fragment coding for the complete intracellular portion of AEV-erbB (H) (Yamamoto, T. et al., 1983 "Cell" 35:71-78) was ligated together with the EGF fragment into a pUC12 plasmid opened with SacI and SmaI. The recombinant plasmid was amplified in E. coli HB101 and the coding region for the complete chimeric receptor is removed in a 3.7 kb SacI-XmnI restriction fragment, both sites being located in the untranslated regions of the EGF receptor and v-erbB sequence, respectively.

p342E (Crowley et al., 1983, "Mol. Cell. Biol." 3:44-55) was digested with EcoRI and the opened plasmid recovered. An adaptor having the sequence EcoRI SacI EcoRI

GAATTCGAGCTC

CTCGAGCTTAAG is ligated with the opened plasmid, the ligation mixture transfected into E. coli 294, and plasmid pCVSVE-HBS having the adaptor insert is recovered from an ampicillin resistant colony.

pCVSVE-HBS is partially digested with SacI and the linearized vector fragment (I) recovered. The linearized plasmid is digested with HpaI and the vector fragment recovered.

The pCVSVE-HBS vector fragment is ligated to the SacIXmnI fragment encoding the hybrid receptor and expression vector pCVSV-HER-erbB was recovered from a transformed E. coli HB101 colony.

EXAMPLE 6

Expression of Receptor-Oncogene Hybrid

Expression vector pCVSVE-HER-erbB is cotransfected into normal Rat 1 fibroblasts together with a neomycin resistable expression plasmid by calcium phosphate coprecipitation based on the protocol of Graham and van der Eb (1973). Subconfluent cells were transfected with 10 μg of plasmid DNA per 8 cm culture dish. DNA was dissolved in 0.55 ml of 1 mM Tris pH 7.5, 0.1 mM EDTA, 250 mM $CaCl_2$ and 0.5 ml of 50 mM HEPES pH 7.12, 280 mM NaCl, 1.5 mM $Na_2HPO_4$ was slowly added. A precipitate gradually formed within 40 min. which was added to the 10 ml of cell culture medium. 5h after transfection, cells were subjected to a glycerol shock treatment by incubation in 3 ml of 20 percent glycerol in PBS for 1 min. The glycerol was washed off and the cells were further cultured in the original medium.

The neomycin resistance gene under the control of the SV40 early promoter was used as a selectable marker. Medium supplemented with 400 μg/ml Geneticin (Sigma G5013) was used for selection starting two days after transfection. Neomycinresistant cells were then grown in medium supplemented with a 200 nM, then 1000 nM concentration of methotrexate (Sigma A6770) containing 7 percent dialyzed fetal bovine serum. The result was a step-wise amplification of cDNA expression in neomycin resistant cell lines.

Expression of the hybrid in the transformants was first monitored by analyzing proteins metabolically labeled with $^{35}S$-methionine after immunoprecipitation of detergent lysates with a human EGF receptor-specific mouse monoclonal antibody R1. Stably expressing cell lines were metabolically labeled with $^{35}S$-methionine. Specific proteins were immunoprecipitated by protein A-Sepharose adsorbed R1 antibody from detergent lysates prepared as described above and analyzed on SDS reducing polyacrylamide gels. The mousse monclonal R1 antibody (Waterfield et al., 1982, "J. Cell. Biochem." 20:149-161) does not recognize the endogenous RatI cell EGF receptor. The HER-erbB protein was readily detected in immunoprecipitates before and after methotrexate amplification. As expected, the HER-erbB protein was smaller than the wild type EGF receptor expressed in A431 cells. When compared with the very high level of EGF receptor expressed in A431 cells, amplified RatI cells expressed only 3-fold less HER-erbB.

The hybrid HER-erbB protein displayed specific EGF binding since $^{125}I$-EGF at various concentrations was bound to transformant cells. The binding was saturable and could be completely displaced in the presence of a 100-fold excess of unlabelled EGF. The amount of binding of $^{125}$I-labeled EGF to confluent RatI cultures corresponded precisely to the amount of EGF receptor or chimeric receptor expressed by the respective cel cultures. Thus the constructed proteins contained fully functional EGF binding domains and were faithfully transported to the cell surface.

EXAMPLE 7

EGF-stimulated in vitro autophosphorylation

To test whether HER-erbB possessed in vitro autophosphorylation activity, cell lysates were immunoprecipitated as described above, incubated with $^{32}$P-$\gamma$-ATP and analyzed by polyacrylamide gel electrophoresis and autoradiography: Transformant cell monolayers grown in 8 cm culture dishes were washed twice with PBS and solubilized as described by Kris et al. "Cell" 40:619-625 (1985). One ml of 50 mM HEPES pH 7.5, 150 mM NaCl, 1.5 mM MgCl$_2$, 1 mM EGTA, 10 percent glyercol, 1 percent Triton X-100, 1 percent Aprotinin and 4$\mu$g/ml phenylmethylsulfony fluoride (PMSF) was added to the monolayers at 4° C. for 5 min. Solubilized cells were centrifuged at 10,000 g for 5 min at 4° C., and the supernatant was either stored at −70° C. or processed further.

EGF stimulation of autophosphorylation was induced by incubating the detergent cell lysates diluted to a 0.5 percent TX-100 concentration in 0.4 ml prior to the immunoprecipitation, with 5 $\mu$g/ml for 15 min at 4° C. R1 antibody prebound for 30 min to protein A-Sepharose was added (1 $\mu$l antibody/50 $\mu$l slurry 1:1), and the incubation continued for 15 min at 4° C. The immunoprecipitates were washed 5 times in 0.9 ml HNTG buffer (20 mM HEPES pH 7.5, 150 mM NaCl, 10 percent glycerol, and 0.1 percent Triton X-100). The washed immunoprecipitates, in a volume of 30 $\mu$l were adjusted to 5 mM MnCl$_2$ and 15 $\mu$Ci of $\gamma$-$^{32}$P-ATP was added for 0.5 min at 4° C. The autophosophorylation reaction was stopped by adding 20 $\mu$l of 3 times concentrated SDS sample buffer. Samples were boiled for 5 min, centrifuged, and 20 $\mu$l aliquots analyzed on 5 percent/7 percent SDS polyacrylamide reducing gels (Laemmli, 1970). Gels were fixed and dried under vacuum at 70° C. Normal RatI fibroblasts were used as a control. Size markers are indicated in kilodaltons. Like the wild type EGF receptor, the HER-erbB hybrid incorporated significant amounts of $^{32}$P in immunoprecipitates. The extent of phosphorylation was increased by the addition of EGF (designated by+); when measured at 30 seconds, the rate of phosphorylation was found to be 3 fold higher in the presence of EGF. The v-erbB protein itself possesses only very low autophosphorylation activity (Lax et al., 1985, "EMBO Journal" 4:3179–3182). Despite the low autophosphorylation activity claimed in the hybrid, reconstitution of the EGF binding domain led to ligand-inducible autophosophorylation activity.

We claim:

1. A hybrid receptor for a ligand comprising (a) a ligand binding domain of a predetermined receptor fused at its C-terminus to the N-terminus of (b) a reporter polypeptide which is (1) heterologous to the receptor from which is obtained the ligand binding domain and which (2) undergoes a conformational change upon the binding of said ligand to the ligand binding domain.

2. The hybrid receptor of claim 1 wherein the ligand binding domain is comprised by the extracellular domain of the predetermined receptor.

3. The hybrid receptor of claim 1 wherein the reporter polypeptide is a cytoplasmic domain of a receptor of an oncogene product.

4. The hybrid receptor of claim 1 wherein the reporter polypeptide is an enzyme.

5. The hybrid receptor of claim 4 wherein the enzyme is a phosphorylkinase.

6. The hybrid receptor of claim 1 having a transmembrane domain interposed between the ligand binding domain and the heterologous reporter polypeptide.

7. The hybrid receptor of claim 1 wherein the ligand binding domain of the predetermined receptor consists essentially of the ligand binding domain of the predetermined receptor.

8. A method for assaying a biologically active ligand or an antagonist or agonist for said ligand, comprising
   (a) providing a hybrid receptor which comprises (1) a binding domain for the ligand, antagonist or agonist and (2) a heterologous reporter polypeptide;
   (b) incubating the receptor with a test sample suspected to contain the ligand, antagonist or agonist;
   (c) detecting a conformational change in the reporter polypeptide; and
   (d) correlating said change with the presence of the ligand, antagonist or agonist in the test sample.

9. The method of claim 8 wherein the ligand is a polypeptide and the ligand binding domain is not the antigen binding site of an immunoglobulin.

10. The method of claim 8 wherein the change in the reporter polypeptide is a modification of the enzymatic activity of the polypeptide.

11. The method of claim 10 wherein the change in the reporter polypeptide is autophosphorylation of the reporter polypeptide.

12. The method of claim 8 for assaying a test sample suspected of containing an antagonist wherein the receptor is incubated with the test sample and a predetermined amount of ligand or ligand agonist.

13. The method of claim 8 wherein the change in the reporter polypeptide is an immunoligical change.

14. The method of claim 8 wherein the reporter polypeptide further comprises a stable free radical, fluroescent or chemiluminescent group and the change in the reporter polypeptide is detected by measuring a change in the rotational moment of the stable free radical or a change in the intensity, wavelength or polarization of the fluorescent or chemiluminescent group.

15. The method of claim 8 wherein the reporter polypeptide is capable of binding to a G protein.

* * * * *